(12) United States Patent
Asmussen et al.

(10) Patent No.: US 8,287,490 B2
(45) Date of Patent: Oct. 16, 2012

(54) DISPOSABLE INJECTOR PROVIDED WITH HIGH INJECTOR SAFETY

(75) Inventors: Bodo Asmussen, Ammersbek (DE); Hans-Rainer Hoffmann, Newwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 58 days.

(21) Appl. No.: 13/065,470

(22) Filed: Mar. 22, 2011

(65) Prior Publication Data

US 2011/0208119 A1 Aug. 25, 2011

Related U.S. Application Data

(63) Continuation-in-part of application No. PCT/EP2009/006065, filed on Aug. 21, 2009.

(30) Foreign Application Priority Data

Sep. 23, 2008 (DE) .......................... 10 2008 048 595

(51) Int. Cl.
*A61M 5/30* (2006.01)
*A61M 5/20* (2006.01)
(52) U.S. Cl. .......................................... 604/68; 604/136
(58) Field of Classification Search ..................... 604/68
See application file for complete search history.

(56) References Cited

U.S. PATENT DOCUMENTS

| 6,517,517 | B1 | 2/2003 | Farrugia et al. |
| 2002/0099329 | A1 | 7/2002 | Castellano |
| 2004/0055662 | A1 | 3/2004 | Neracher |
| 2006/0264830 | A1* | 11/2006 | Hommann ................... 604/136 |
| 2008/0146997 | A1 | 6/2008 | Hoffmann |
| 2010/0106090 | A1* | 4/2010 | Matusch ...................... 604/135 |

FOREIGN PATENT DOCUMENTS

| EP | 1 336 419 A1 | 8/2003 |
| WO | WO 94/11041 | 5/1994 |
| WO | WO 95/03844 | 2/1995 |
| WO | WO 97/13537 | 4/1997 |
| WO | WO 01/41847 A2 | 6/2001 |

* cited by examiner

*Primary Examiner* — Nicholas Lucchesi
*Assistant Examiner* — Jason Flick
(74) *Attorney, Agent, or Firm* — R. S. Lombard; K. Bach

(57) ABSTRACT

The invention relates to a needle-less, disposable injector comprising a housing (10), which has at least one compression bar, a cylinder-piston unit (100), a plunger-actuating ram (60), a trigger unit (80) and a spring energy reservoir (50), wherein the trigger unit locks the pre-tensioned spring energy reservoir by means of the compression bar. During triggering, the compression bar slides along at least one trigger element (82) of the trigger unit and, after triggering the trigger unit, the spring energy reservoir displaces the compression bar by means of the plunger-actuating ram and actuates the cylinder-piston unit. When loaded by the pre-tensioned spring energy reservoir, the pairing formed by the mutually facing inner wall of the trigger element and the contact surface of the compression bar has at least in areas a higher sliding friction coefficient than the pairing formed by the mutually facing collar surface of the plunger-actuating ram and the support surface of the compression bar. The present invention provides a disposable injector where the required minimum contact-pressure force is ensured during use thereof.

7 Claims, 3 Drawing Sheets

US 8,287,490 B2

DISPOSABLE INJECTOR PROVIDED WITH HIGH INJECTOR SAFETY

CROSS-REFERENCE TO RELATED APPLICATION

This is a continuation-in-part application of pending international application PCT/EP2009/006065 filed Aug. 21, 2009 and claiming the priority of German Application No. 10 2008 048 595.0 filed Sep. 23, 2008.

BACKGROUND OF THE INVENTION

The invention relates to a single-use injector with a housing comprising at least one press rod, with a cylinder/piston unit, with a piston actuating plunger, with a triggering unit and with a spring energy store, the triggering unit initially interlocking the pre-tensioned spring energy store by means of the press rod, the press rod sliding, on triggering, along at least one triggering element of the triggering unit and, after triggering of the triggering unit, the spring energy store displacing the press rod and actuating the cylinder/piston unit by means of the piston actuating plunger.

A single-use injector of this type is known from the subsequently published DE 10 2007 034 871. If this injector is exposed with too little pressure acting on the injection site, there is the risk that injection solution will escape in the lateral direction relative to the axis of the injection jet. This leads to what is known as a wet shot.

EP 1 336 419 A1 discloses a jet injector comprising a housing, a fluid chamber, a piston, a force-generating source, an activation element for activating the force-generating source and a needle protection which is arranged at the distal end of the housing for covering a needle.

U.S. 2002/0099329 A1 discloses a gas operated needleless injection device wherein, by an axial displacement of a cap, a hollow needle is pressed into a gas cartridge.

DE 10 2005 062 206 B3 discloses a single-use injector with a housing in which at least a mechanical spring energy store, at least one cylinder-piston unit which can at least temporarily be filled with an effective substance, at least a piston operating plunger and at least a release unit are arranged. Herein, the spring energy store comprises a pre-tensioned spring element which is held in a pre-tensioned position by a pull means which at least partially extends around the spring element. The release unit further comprises a cutting tool which, for the release of energy of the spring energy store, severs or weakens the pull means at at least one location wherein weakening causes an immediate rupture of the pull means.

The object of the present invention is therefore based on the problem of developing a single-use injector, use of which ensures the required minimum contact force.

SUMMARY OF THE INVENTION

The invention relates to a needle-less, disposable injector comprising a housing (10), which has at least one compression bar, a cylinder-piston unit (100), a plunger-actuating ram (60), a trigger unit (80) and a spring energy reservoir (50), wherein the trigger unit locks the pre-tensioned spring energy reservoir by means of the compression bar. During triggering, the compression bar slides along at least one trigger element (82) of the trigger unit and, after triggering the trigger unit, the spring energy reservoir displaces the compression bar by means of the plunger-actuating ram and actuates the cylinder-piston unit. When loaded by the pre-tensioned spring energy reservoir, the pairing formed by the mutually facing inner wall of the trigger element and the contact surface of the compression bar has at least in areas a higher sliding friction coefficient than the pairing formed by the mutually facing collar surface of the plunger-actuating ram and the support surface of the compression bar. The present invention provides a disposable injector where the required minimum contact-pressure force is ensured during use thereof.

BRIEF DESCRIPTION OF THE DRAWINGS

Further details of the invention will emerge from the following schematically illustrated embodiments, in which.

DETAILED DESCRIPTION OF THE PARTICULAR EMBODIMENTS

Figure 1:
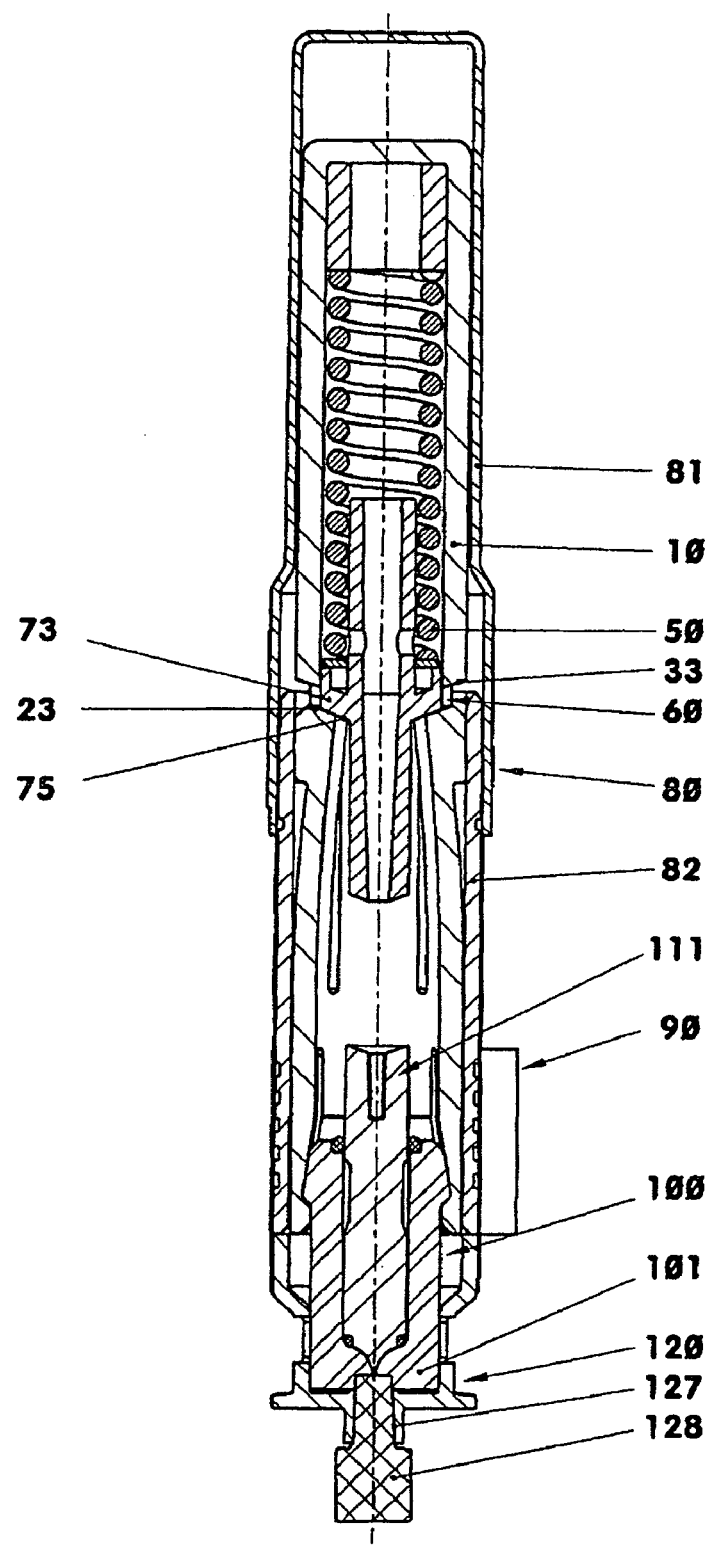
FIG. 1 shows a needle-less single-use injector with two press rods deformed in the locking position.
Figures 2, 3:
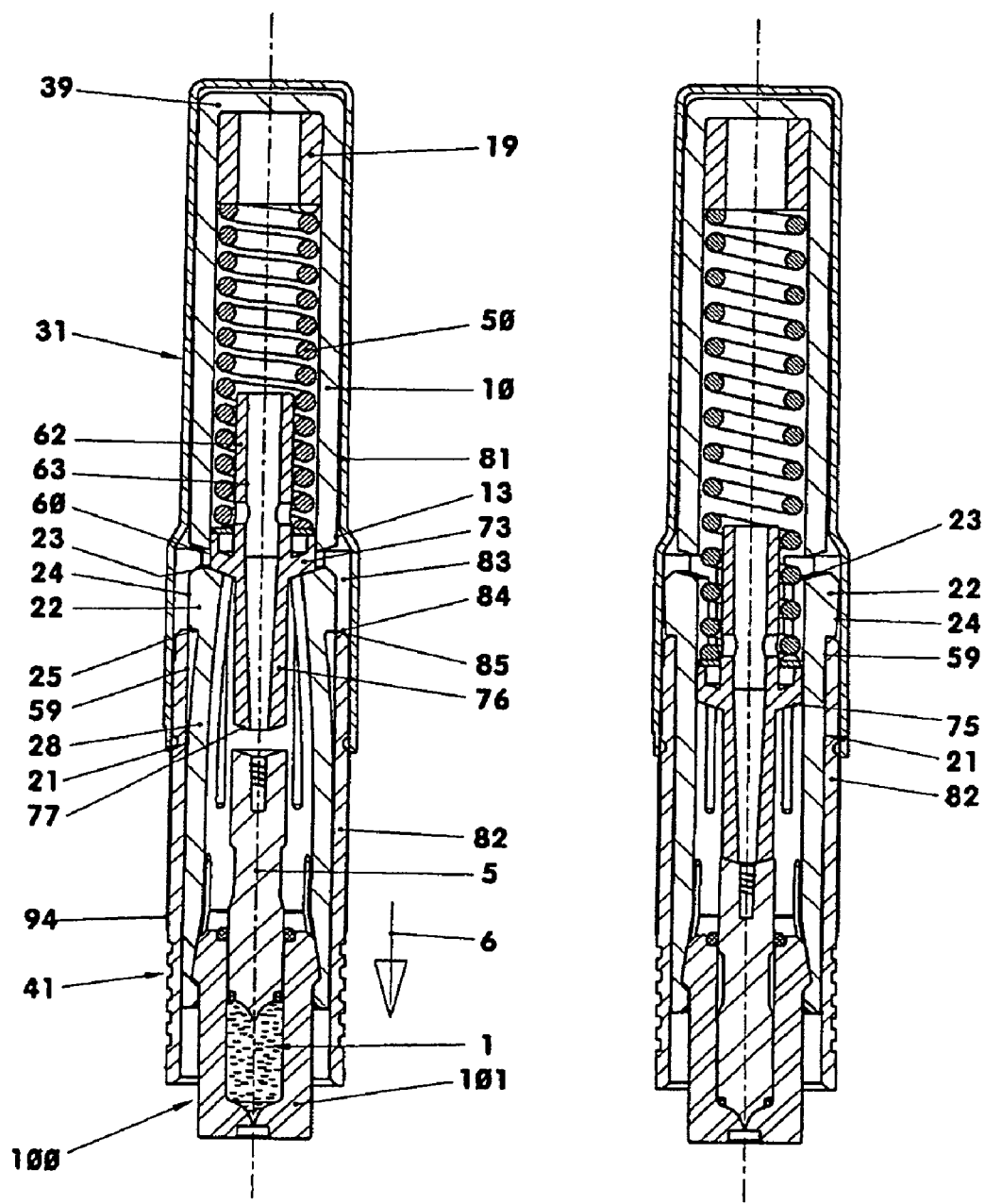
FIG. 2 shows the single-use injector during triggering.
FIG. 3 shows the single-use injector after triggering.

FIGS. 1 to 3 show a single-use injector in three different triggering states. FIG. 1 shows the single-use injector prior to filling and triggering. FIG. 2 shows the single-use injector during triggering and FIG. 3 shows it after triggering.

The single-use injector illustrated in FIGS. 1-3 consists of a housing (10), a cylinder/piston unit (100), a piston actuating plunger (60) and a helical compression spring (50) as the spring energy store. In addition, a triggering unit (80) with a triggering element (82) and a securing element (90) are arranged on the housing (10). In the illustration of FIG. 1, the cylinder/piston unit (100) is closed at the front by means of a closure cap (120) in combination with a stopper (128).

The housing (10) is a one-piece, pot-shaped, downwardly open hollow body with an elevated floor (39). The housing is made, for example, from a glass fibre-reinforced polyamide by injection-moulding. The housing (10) has a substantially tubular form and is divided into two functional regions: on the one hand, the upper envelope region (31) and, on the other hand, the lower fixing region (41).

In the envelope region (31), the housing (10) has, for example, two mutually opposing, window-like apertures (33). A respective press rod (21), as a resilient bending bar, is moulded onto the lower edge of the individual aperture (33). The moulding-on site for the press rods (21) is positioned just above the fixing region (41). For forming each press rod (21), a narrow, at least roughly U-shaped gap, which surrounds the individual press rod (21) to the side and top, is located in the lower region of the envelope portion (31).

The press rod (21) has, for example over 80% of its length, the wall thickness and the curvature of the wall of the housing (10). This region has inter alia also the function of a resilient bending bar (28). It has a crescent-shaped cross section.

If appropriate, a portion of this bending bar (28) can also be equipped with a rectangular cross section in order to reduce bending stresses which occur during use in the edge region of the bending bar.

In the case of injectors in which the piston actuating plunger (60) is—at least in certain portions—guided straight with a low degree of play in the housing (10) and the piston actuating plunger (60) has sufficient bending strength, use may also be made of just a single press rod (21) instead of two or more press rods (21).

The—in this case—upper free end of the individual press rod (21) is formed by the radially outwardly protruding cam (22). The cam has at least one support surface (23) oriented in the direction of the centre line (5) and an abutment surface (24) facing away from the centre line (5).

Holding elements for fastening the cylinder/piston unit (100) are located in the lower region of the housing (10). In the exemplary embodiment, the cylinder/piston unit (100) consists of a transparent cylinder (101) which can be filled with an injection solution (1). In the illustration of FIG. 1, the piston (111) is in the front position. Above the piston (111), the piston actuating plunger (60) is, for example, arranged in the housing (10) in such a way that, although it does not touch the piston (111), it is laterally guided by its lower end, for example in the upper region of the cylinder (101).

The lower half of the housing (10) is surrounded by the sleeve-like triggering element (82). The triggering element is, for example, embodied in a substantially cylindrical manner and made, for example, of acrylonitrile butadiene styrene (ABS) copolymer. The triggering element (82) is longitudinally displaceably mounted on the radial outer surface (13) of the housing (10). It ends rearwardly with a sharp edge (85) which is part of an end-side, set-back flank (84) of the triggering element (82). According to FIG. 1, below the edge (85), the outward abutment surfaces (24) of the cams (22), which are moulded onto the press rods (21), touch the inner wall (59) of the triggering element (82) in a securing manner.

For example, close to the edge (85), a triggering cap (81), which completely surrounds the trailing end of the housing (10), is fastened to the triggering element (82). The triggering cap (81) comprises a peripheral widening (83) in which the cams (22) are received on triggering of the injector, cf. FIG. 3. In the case of a non-rotationally symmetrical triggering element (82), partial widenings or non-covered openings may also be present for each press rod (21), instead of this widening (83). Above the widening (83), the triggering cap (81) rests against the outer wall (13) of the housing (10) in a slidable manner.

The closure cap (120) adjoins the leading end of the triggering element (82). The closure cap encases the lower part of the cylinder/piston unit (100). The closure cap (120) has, on the leading end side, an adapter opening (127) with, for example, a Luer inner cone which is closed in a sterile manner by means of an outer conical stopper (128). The closure cap (120) is in this case mounted on the lower region of the housing (10).

The piston actuating plunger (60), which is arranged in the housing (10), is divided into two regions. The lower region is the piston slide (76). Its diameter is somewhat smaller than the internal diameter of the rear region of the cylinder (101). The lower end face of the piston slide (76) acts directly on the piston (111).

The upper region of the piston actuating plunger (60), the plunger plate (73), is a flat disc which is cylindrical at least in certain regions and the external diameter of which is smaller by a few tenths of a millimetre than the internal diameter of the housing (10) in the envelope region (31). The lower end side has a collar surface (75) which is arranged around the piston slide (76). The collar surface has the shape of a frustoconical envelope, the apex angle of which is approx. 100 to 140 degrees. In the illustrated exemplary embodiment, the collar surface (75) has an apex angle of 140 degrees. The notional apex of the frustoconical envelope rests on the centre line (5) in the region of the piston slide (76). The collar surface (75) can also be spherically curved.

Obviously, the piston slide (76) may also be embodied as a separate component in isolation from the plunger plate (73). For this purpose, the piston slide is then guided on the inner wall of the housing (10).

The helical compression spring (50) sits pre-tensioned between the plunger plate (73) and the elevated floor (39) of the housing (10). The helical compression spring (50) is supported on the elevated floor (39) of the housing (10), a spacer sleeve (19) being interposed. The spring force of the helical compression spring (50) is transmitted to the press rods (21) via the plunger plate (73). Owing to the inclination of the collar surface (75), the press rods (21) are urged radially outward in the manner of a wedge gear. The triggering sleeve (82) permanently supports this radial force.

The piston actuating plunger (60) has a guide pin (62) above the plunger plate (73). The guide pin guides the helical compression spring (50) or is guided thereby. The piston slide (76), which acts on the piston (111) on actuation of the single-use injector, is located below the plunger plate (73), centrally in the extension of the guide pin (62). The piston slide (76) has an envelope of a cone-shaped, forwardly arched end face (77), cf. inter alia FIG. 2. With this end face (77), the piston slide contacts, on triggering, the complementarily shaped end face of the piston (111), cf. FIG. 3. Both cones have at least roughly the same cone angle.

Before the single-use injector is filled and used, the spring energy store (50) is pre-tensioned, cf. FIG. 1. The two pressure-loaded press rods (21) hold the piston actuating plunger (60), on the plunger plate (73) thereof, in its pre-tensioned position. For this purpose, the support surfaces (23) of the press rods (21) are supported on the plunger plate (73). The size of each area of contact between a support surface (23) and the corresponding location on the plunger plate (73) is in the range of from 2 to 20 mm$^2$. Both the support surface (23) and the collar surface (75), which faces the support surface and with which it forms a pairing, have for example a mean roughness value which is smaller than ten micrometres. For example, the mean roughness value is six micrometres.

The flexural elasticity of the press rods (21) and the plunger plate (73) press the support rods (21) at least approximately radially outward against the triggering element (82). There, they rest against the triggering element (82) via cams (22). The cams (22) can in this case also be positioned, for example, 5 to 20 millimetres below the respective free upper end of the press rods (21).

Figure 4:
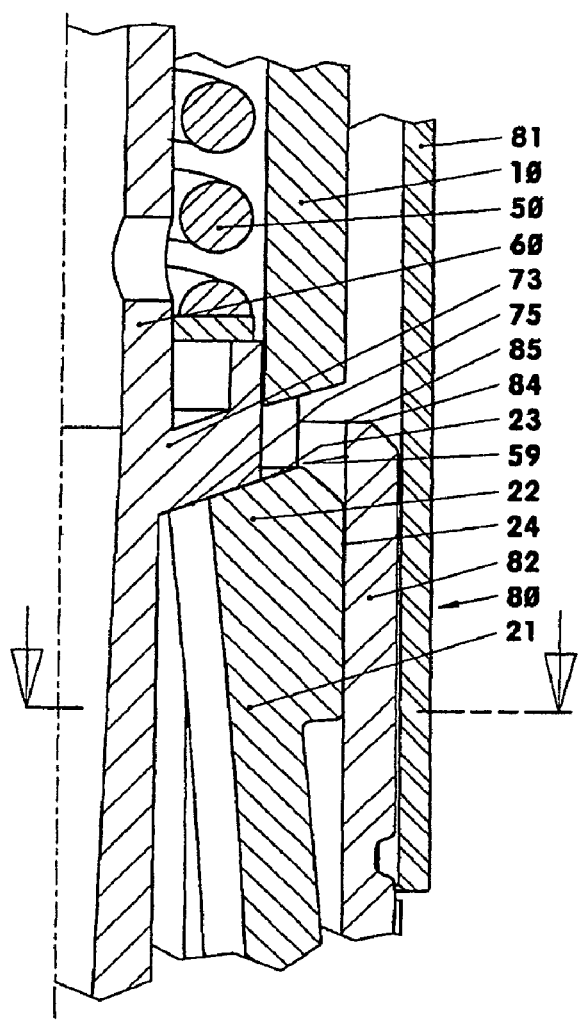
FIG. 4 shows a detail from FIG. 1.

According to FIGS. 1 and 4, the plunger plate (73) of the tensioned single-use injector rests on the support surface (23) via its collar surface (75). The support surface (23), which in this case performs the function of a wedge surface, has the shape of a frustoconical envelope having an apex angle of 140 angular degrees.

If appropriate, the press rods (21) or the collar surface (75) have a ceramic armouring, at least in the contact region. The collar surface (75) can be reinforced by a, for example adhesively bonded-on, frustoconical envelope-shaped washer.

The abutment surface (24) of the cams (22) is part of a cone, the maximum diameter of which is, for example, 3 to 4 millimetres larger than the external diameter of the housing (10). When the single-use injector is tensioned, the abutment surface (24) contacts the inner wall (59) of the sleeve-like triggering element (82). The contact region is shown enlarged in FIG. 4. Accordingly, the abutment surface (24) is pressed, owing to the bending of the individual press rod (21), above all in its lower region, against the inner wall (59) of the triggering element (82). The abutment surface (24) may be structured or roughened. For example, it can have flutes arranged, in a plan view of an unwinding of the abutment surface (24), in the transverse direction, cf. FIG. 6, or a diamond pattern, cf. FIG. 7. These patterns are arranged, for example, uniformly. The mean roughness value of the abutment surface (24) is, for example, greater than ten micrometres.

Figure 5:
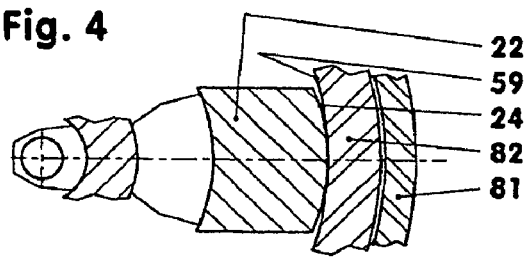
FIG. 5 is a section through FIG. 4.
Figure 7:
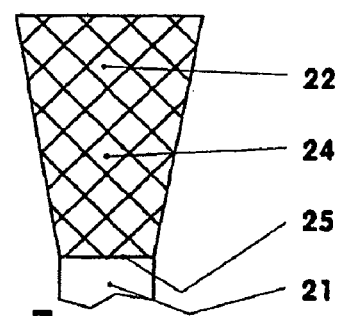
FIG. 7 shows a variant to FIG. 5.

In the illustration of FIG. 7, the width of the abutment surface (24) of the individual press rod (21) grows from the bottom up. Thus, the pressure pressing the abutment surface (24) against the inner wall (59) is higher in the lower region than in the upper. In order to intensify this effect, the abutment surface (24) can have a smaller radius than the inner wall (59) in the transverse direction, cf. FIG. 5. The width of the contact surface may therefore be smaller than the width of the individual press rod (21).

In order to be able to use the single-use injector, the cylinder/piston unit (100) must first be filled. For this purpose, the stopper (128) is removed from the adapter opening (127) and an injection solution (1) is, for example, pressed in or drawn in. The piston (111) is in this case pressed back or drawn back.

In order to release the injector, the securing element (90), for example a tear-off banderole (94), is withdrawn, so that the adhesive connection between the closure cap (120) and the triggering element (82) is cancelled. The closure cap (120) is withdrawn. The single-use injector is positioned on the injection site. The spring energy store (50) is tensioned; the press rods (21) continue to support the collar surface (75) of the plunger plate (73).

Now, the triggering element (82) can be displaced in the direction of the cylinder/piston unit (100), cf. FIG. 2. The state illustrated in FIG. 2 is not static; it will therefore be designated hereinafter as a fictitious state.

On triggering of the single-use injector, the triggering element (82) slides on the outer wall (13) of the housing (10), in the triggering movement direction (6), linearly downward, i.e. in the direction of the injection site. The abutment surfaces (24) of the press rods (21) slip via the edge (85). The press rods (21) bend resiliently outward into their actual starting position and jump, under the force of the spring element (50), radially outward into the widening (83).

In relation to the housing (10), the widening (83) is precisely positioned and configured in such a way that it can receive the press rods (21), which are urged outward and recede during the triggering process, with their cams (22). The inner contour of the widening (83) is, for example, a channel with a set-back flank (84) which is in this case a plane normal to the centre line (5) of the injector. As soon as the cams (22) are displaced into the widening, the piston actuating plunger (60) shoots unimpeded downward, cf. FIG. 3. The piston (111) is pressed downward. The cylinder (100) is drained.

Figure 6:
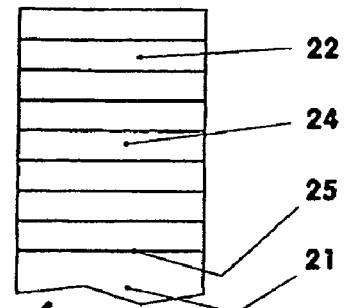
FIG. 6 is a plan view of the unwinding of an abutment surface.

The inner wall (59) of the triggering element (82) is, for example, roughened or structured in the region along which the abutment surface (24) slides. The roughness values correspond, for example, to the roughness values of the abutment surface (24). In the case of a structure, the pattern can be embodied such as it is illustrated in FIG. 6 or 7.

Figure 8:
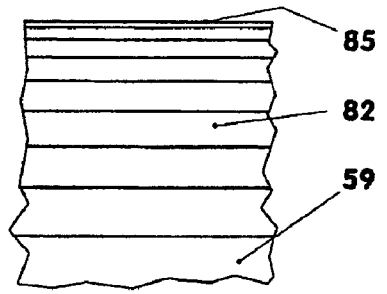
FIG. 8 is a view of the unwinding of an inner wall.
Figure 9:
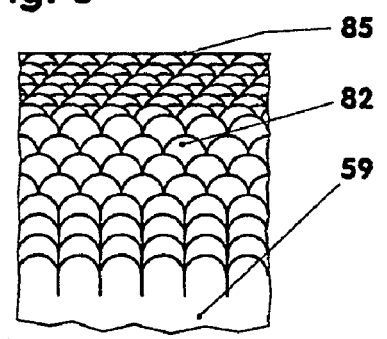
FIG. 9 shows a variant to FIG. 8.

However, the structural density and/or the roughness of the inner wall (59) can also increase with the stroke of the movement of the abutment surface (24) relative to the inner wall (59) of the triggering element (82). FIG. 8 is, for example, a greatly enlarged view of a structural pattern which adjoins the sharp-edged edge (85) and has mutually parallel slots, the distance between which decreases from the bottom up. FIG. 9 shows a scale pattern, the scales of which can be positive and/or negative in their embodiment. The distance between the scales increases in the direction of relative movement— from the bottom up. The lowest region of the contact surface of the inner wall (59), against which the abutment surface (24) rests prior to triggering, is, for example, structure-free.

Prior to triggering and during triggering of the single-use injector, the helical spring (50) presses the cams (22) outward via the plunger plate (73). Owing to the low coefficient of sliding friction resulting from the large area of contact and the low surface roughness of the pairing of the collar surface (75) and the support surface (23), this wedge gear has high efficiency.

In order to trigger the single-use injector once it has been placed onto the injection site, the operator must first overcome the adhesive friction, caused inter alia by the contact force, between the abutment surface (24) and the inner wall (59). The smaller the area of contact of the pairing and the higher the surface roughness, the higher this adhesive friction is.

Therefore, the higher the adhesive frictional force is, the more intensively the user will press the single-use injector against the injection site. Thus, in the static state, a high roughness value of the pairing of the abutment surface (24) and the inner wall (59) ensures that the user continues to press the single-use injector, once positioned, against the injection site with a minimum force.

As soon as the user has overcome the adhesive frictional force during triggering, the inner wall (59) of the triggering element (82) slides along the abutment surfaces (24). The coefficient of sliding friction of the pairing of these two surfaces (24, 59) is dependent on the materials involved, the surface roughness and/or the surface structure and the surface pressure. The coefficient of sliding friction of this pairing is greater than the coefficient of sliding friction of the pairing formed by the collar surface (75) and the support surface (23). If, for example, the abutment surface (24) and the inner wall (59) are embodied with a structure according to FIG. 6, an approximately constant, high feed force is, for example, required for displacing the triggering element (82). The user will therefore continue to press the single-use injector against the injection site with a force which is equal to or greater than the press-in force required for a safe injection.

The user has to apply this force until the rear grip flank (25) has reached the edge (85). Owing to the low sliding friction of the pairing formed by the collar surface (75) and the support surface (23) and to the small wedge angle, the cams (22) are abruptly displaced into the widenings (83).

On triggering of a single-use injector, the inner wall (59) of which has, for example, a structure according to FIG. 8, the force required for triggering increases during the displacing of the triggering element (82). The user is thus forced to press the single-use injector increasingly intensively against the injection site. This ensures that, when the spring energy is released, the single-use injector is pressed against the injection site so forcefully that a wet shot is prevented.

The feed force of the triggering element (82) required to overcome the adhesive friction may be less than the feed force required to overcome the sliding friction. For this purpose, the inner wall (59) may, for example, be embodied as illustrated in FIG. 9. The region of the inner wall (59) in which the abutment surface (24) abuts prior to triggering has in this case, for example, low surface roughness. As soon as the abutment surface (24) has left this region, the roughness, and thus the coefficient of sliding friction, rises. For example, the user may in this way be forced to apply a uniform or linearly rising force for the purposes of triggering. At least the feed force which has to be applied immediately prior to the jumping-out of the cams (22) is equal to or greater than the minimum contact force required for a safe injection.

If appropriate, the material of the piston actuating plunger (60), the pressure rods (21) and the triggering element (82) may be identical.

In the variants illustrated in the figures, the sole zone of contact between the press rod (21) and the plunger plate (73) is embodied as surfaces (23) and (75) which contact each other in a slidable manner. In one particular configuration, a roller, which, on actuation of the injector, rolls off the surface (75) of the plunger plate in a roller-mounted, i.e. low-friction, manner, can be mounted in each surface (23) of the individual press rods (21).

A helical movement may also be provided instead of a linear sliding movement of the triggering element (82) on the housing (10). In this case, the triggering element (82) and the housing (10) are guided one on the other, for example via a connecting link and a link block. If appropriate, the triggering can also be implemented by a pure pivoting movement between the housing (10) and the triggering element (82). The pivot axis would in this case be the centre line (5).

Obviously, it is also conceivable to combine the various aforementioned embodiments with one another.

LIST OF REFERENCE NUMERALS

1 Injection solution; medicament
5 Centre line of the injector, longitudinal direction
6 Triggering movement direction of (82), downward movement direction arrow
10 Housing, one-piece
13 Outer surface, cylindrical
19 Spacer sleeve
21 Press rods, support rods; pull hooks
22 Cams
23 Support surface
24 Abutment surface
25 Rear grip flank
28 Bending bar
31 Envelope region
33 Apertures
39 Floor
41 Fixing region for the cylinder/piston unit
50 Spring element, helical compression spring, spring energy store
59 Inner wall of (82)
60 Piston actuating plunger
62 Guide pin
63 Hole, through-hole
73 Plunger plate
75 Collar surface, conical
76 Piston slide
77 Piston end face, envelope of a cone-shaped
80 Triggering unit
81 Triggering cap
82 Triggering element
83 Widening
84 Set-back flank
85 Edge, sharp-edged
90 Tamper-proof closure, banderole, securing element
94 Tear-off banderole
100 Cylinder/piston unit
101 Cylinder
111 Piston
120 Closure cap, adhesive sealing
127 Adapter opening
128 Stopper

What is claimed is:

1. In combination with a needle-less single-use injector with a housing (10) comprising at least one press rod (21), a cylinder/piston unit (100), a piston actuating plunger (60) having a collar surface (75), a triggering unit (80) and a pre-tensioned spring energy store (50), the triggering unit (80) initially interlocking the pre-tensioned spring energy store (50) by means of the at least one press rod (21), the at least one press rod (21) is slidably moveable and is displaceable, on triggering, by means of the spring energy store (50) and the piston actuating plunger (60), along at least one triggering element (82) of the triggering unit (80) and, the triggering unit (82) having an inner wall (59), the at least one press rod (21) having an abutment surface (24) in slidable contacting and displaceable relationship on triggering with the inner wall (59) to form a mutually facing pairing and a support surface (23) in slidable temporary contacting relationship on triggering with the collar surface (75) to form a mutually facing pairing, after triggering of the triggering unit (80), the spring energy store (50) displacing the at least one press rod (21) and actuating the cylinder/piston unit (100) by means of the piston actuating plunger (60), the improvement which comprises:

when loaded by the pre-tensioned spring energy store (50), the pairing of the mutually facing inner wall (59) of the triggering element (82) and the abutment surface (24) of the at least one press rod (21) is provided, with at least in certain regions, a higher coefficient of sliding friction than the pairing of the mutually facing collar surface (75) of the piston actuating plunger (60) and the support surface (23) of the at least one press rod (21).

2. The combination according to claim 1, wherein in that the triggering element (82) surrounds the housing (10) in a sleeve-like manner, at least in certain regions.

3. The combination according to claim 1, wherein the housing (10) comprises two press rods (21).

4. The combination according to claim 1, wherein the abutment surface (24) and/or the inner wall (59) have a mean roughness value greater than or equal to ten micrometres, at least in the region of contact of the surfaces (24, 59).

5. The combination according to claim 1, wherein the triggering element includes a sharp-edged edge (85), the inner wall (59) of the triggering element (82) has a roughness and/or structural density which increases in the direction of a sharp-edged edge (85) of the triggering element (82).

6. The combination according to claim 1, wherein the width of the abutment surface (24) used is smaller than the width of the individual press rod (21).

7. The combination according to claim 4, wherein the abutment surface (24) and/or the inner wall (59) carry patterns or structures incorporated thereon to increase roughness.

* * * * *